United States Patent
Savage

(10) Patent No.: US 9,546,195 B2
(45) Date of Patent: *Jan. 17, 2017

(54) HYDROPHOBIC CERAGENIN COMPOUNDS AND DEVICES INCORPORATING SAME

(71) Applicant: Paul B. Savage, Mapleton, UT (US)

(72) Inventor: Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/602,499

(22) Filed: Jan. 22, 2015

(65) Prior Publication Data

US 2015/0140063 A1    May 21, 2015

Related U.S. Application Data

(63) Continuation of application No. 13/554,957, filed on Jul. 20, 2012, now Pat. No. 8,975,310.

(60) Provisional application No. 61/572,714, filed on Jul. 20, 2011, provisional application No. 61/642,431, filed on May 3, 2012, provisional application No. 61/930,580, filed on Jan. 23, 2014, provisional application No. 61/945,681, filed on Feb. 27, 2014.

(51) Int. Cl.

| | | |
|---|---|---|
| A61K 31/56 | (2006.01) | |
| A61F 13/00 | (2006.01) | |
| C07J 51/00 | (2006.01) | |
| C07J 41/00 | (2006.01) | |
| A61L 27/52 | (2006.01) | |
| A61L 27/54 | (2006.01) | |
| A61L 31/14 | (2006.01) | |
| A61L 31/16 | (2006.01) | |
| A61L 27/34 | (2006.01) | |
| A61L 29/08 | (2006.01) | |
| A61L 29/14 | (2006.01) | |
| A61L 29/16 | (2006.01) | |
| A61L 31/10 | (2006.01) | |
| C07C 211/00 | (2006.01) | |
| A61L 27/18 | (2006.01) | |

(52) U.S. Cl.
CPC .......... *C07J 41/0055* (2013.01); *A61L 27/18* (2013.01); *A61L 27/34* (2013.01); *A61L 27/52* (2013.01); *A61L 27/54* (2013.01); *A61L 29/085* (2013.01); *A61L 29/145* (2013.01); *A61L 29/16* (2013.01); *A61L 31/10* (2013.01); *A61L 31/145* (2013.01); *A61L 31/16* (2013.01); *C07C 211/00* (2013.01); *A61L 2300/208* (2013.01); *A61L 2300/404* (2013.01); *A61L 2300/606* (2013.01)

(58) Field of Classification Search
None
See application file for complete search history.

(56) References Cited

U.S. PATENT DOCUMENTS

| | | | |
|---|---|---|---|
| 4,661,341 A | 4/1987 | Benedict et al. | |
| 4,842,593 A | 6/1989 | Jordan et al. | |
| 4,865,855 A | 9/1989 | Hansen et al. | |
| 4,972,848 A | 11/1990 | Di Domenico | |
| 5,025,754 A | 6/1991 | Plyler | |
| 5,286,479 A | 2/1994 | Garlich et al. | |
| 5,310,545 A | 5/1994 | Eisen | |
| 5,356,630 A | 10/1994 | Laurencin et al. | |
| 5,364,650 A | 11/1994 | Guthery | |
| 5,380,839 A | 1/1995 | McCall et al. | |
| 5,552,057 A | 9/1996 | Hughes et al. | |
| 5,721,359 A | 2/1998 | Dunn et al. | |
| 6,117,332 A | 9/2000 | Hatch et al. | |
| 6,228,393 B1 | 5/2001 | DiCosmo et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,673,771 B1 | 1/2004 | Greene et al. | |
| 6,767,904 B2 | 7/2004 | Savage et al. | |
| 6,803,066 B2 | 10/2004 | Traeder et al. | |
| 6,872,303 B2 | 3/2005 | Knapp et al. | |
| 6,939,376 B2 | 9/2005 | Shulze et al. | |
| 7,282,214 B2 | 10/2007 | Wilcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |
| 7,754,705 B2 | 7/2010 | Savage et al. | |
| 7,854,941 B2 | 12/2010 | Urban et al. | |
| 7,993,903 B2 | 8/2011 | Hayakawa et al. | |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

Roohi et al. Preparation, quality control and biological evaluation of 99mTc-labelled cationic steroid antibiotic (CSA-13), Radiochim. Acta 97, 57-62 (2009).*
Zanger et al., "Structure-Activity Relationship and Drug Design", Remington's Pharmaceutical Sciences, Chapter 27, 16th Edition, 1980, pp. 420-425.
U.S. Appl. No. 13/783,007, filed Mar. 1, 2013, Savage.
U.S. Appl. No. 14/364,283, filed Jul. 29, 2014, Vazquez et al.
U.S. Appl. No. 14/602,071, filed Jan. 21, 2015, Savage.
U.S. Appl. No. 14/624,200, filed Feb. 17, 2015, Savage.
U.S. Appl. No. 14/642,905, filed Mar. 10, 2015, Darien et al.
U.S. Appl. No. 14/644,946, filed Mar. 11, 2015, Beus et al.

(Continued)

*Primary Examiner* — Susannah Chung
*Assistant Examiner* — Robert T Butcher
(74) *Attorney, Agent, or Firm* — Workman Nydegger

(57) ABSTRACT

A hydrophobic cationic steroidal anti-microbial (ceragenin) compound forms an amphiphilic compound having a hydrophobic sterol face and a hydrophilic cationic face. The hydrophobic CSA also includes a hydrophobic substituent that gives the ceragenin compound a C Log P value of at least 6.0, 6.25, 6.5, 7.5, 8.5, or 10.

20 Claims, 9 Drawing Sheets

(56) References Cited

U.S. PATENT DOCUMENTS

| | | | |
|---|---|---|---|
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 2002/0091278 A1 | 7/2002 | Savage et al. |
| 2003/0099717 A1 | 5/2003 | Cabrera |
| 2004/0009227 A1 | 1/2004 | Yao |
| 2004/0058974 A1 | 3/2004 | Courtney et al. |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0252781 A1 | 10/2009 | Sawhney et al. |
| 2009/0324517 A1 | 12/2009 | Kline |
| 2010/0226884 A1 | 9/2010 | Chang et al. |
| 2010/0330086 A1 | 12/2010 | Savage et al. |
| 2011/0091376 A1 | 4/2011 | Savage |
| 2011/0123624 A1 | 5/2011 | Zasloff |
| 2012/0088733 A1 | 4/2012 | Kim et al. |
| 2012/0107382 A1 | 5/2012 | Savage et al. |
| 2013/0022651 A1 | 1/2013 | Savage |
| 2013/0053507 A1 | 2/2013 | Savage |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0315873 A1 | 10/2014 | Beus et al. |
| 2014/0336131 A1 | 11/2014 | Savage et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2015/0203527 A1 | 7/2015 | Savage |
| 2015/0239928 A1 | 8/2015 | Savage |
| 2015/0258123 A1 | 9/2015 | Savage et al. |
| 2016/0193232 A1 | 7/2016 | Beus et al. |
| 2016/0199390 A1 | 7/2016 | Beus et al. |

FOREIGN PATENT DOCUMENTS

| | | |
|---|---|---|
| EP | 0341951 | 11/1989 |
| EP | 1208844 | 5/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | 9524415 | 9/1995 |
| WO | 9944616 | 9/1999 |
| WO | 0042058 | 7/2000 |
| WO | 0214342 | 2/2002 |
| WO | WO02067979 | 9/2002 |
| WO | 03015757 | 2/2003 |
| WO | 03090799 | 11/2003 |
| WO | WO2004082588 | 9/2004 |
| WO | 2004112852 | 12/2004 |
| WO | 2007089903 | 8/2007 |
| WO | 2007089906 | 8/2007 |
| WO | 2007089907 | 8/2007 |
| WO | 2007134176 | 11/2007 |
| WO | WO2008048340 | 4/2008 |
| WO | 2008038965 | 4/2009 |
| WO | 2009079066 | 6/2009 |
| WO | WO2010006192 | 1/2010 |
| WO | 2010036427 | 4/2010 |
| WO | 2010062562 | 6/2010 |
| WO | WO2011066260 | 6/2011 |
| WO | 2011109704 | 9/2011 |
| WO | 2012061651 | 5/2012 |
| WO | 2013029055 | 2/2013 |
| WO | 2013029059 | 2/2013 |
| WO | WO2013040269 | 3/2013 |
| WO | 2013109236 | 7/2013 |

OTHER PUBLICATIONS

U.S. Appl. No. 14/645,040, filed Mar. 11, 2015, Savage et al.
U.S. Appl. No. 14/694,028, filed Apr. 23, 2015, Beus et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureus*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/OI0062704/suppl file/ ol0062704 sl.pdf.

(56) References Cited

OTHER PUBLICATIONS

Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, Mailed Date: Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, Mailed Date: Jul. 24, 2013.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai, et al., " Ceragenins: Cholic Acid-Based Mimics of Antimicrobial peptides", Account of Chemical Research vol. 41, No. 10, Oct. 21, 2008, pp. 1233-1240.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.
U.S. Appl. No. 13/554,930, filed Jul. 20, 2012, Office Action dated Jul. 11, 2014.
U.S. Appl. No. 13/783,131, filed Mar. 1, 2013, Office Action dated Oct. 23, 2014.
U.S. Appl. No. 13/000,010, filed Jun. 16, 2009, Restriction Requirement dated Dec. 4, 2012.
U.S. Appl. No. 13/288,902, filed Jun. 21, 2012, Restriction Requirement dated Jun. 21, 2012.
U.S. Appl. No. 13/288,902, filed Jun. 21, 2012, Office Action dated Nov. 7, 2012.
U.S. Appl. No. 13/288,902, filed Jun. 21, 2012, Notice of Allowance dated Aug. 9, 2013.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
U.S. Appl. No. 14/056,122, filed Oct. 17, 2013, Office Action dated Sep. 3, 2014.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/873,013, filed Oct. 1, 2015, Savage et al.
U.S. Appl. No. 14/926,738, filed Oct. 29, 2015, Vazquez et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/830,356, filed Aug. 19, 2015, Savage.
U.S. Appl. No. 14/866,213, filed Sep. 25, 2015, Savage.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 20.
International Search Report for PCT Application No. PCT/US2013/065510 dated Apr. 30, 2015.
International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

(56) References Cited

OTHER PUBLICATIONS

U.S. Appl. No. 15/135,928, filed Apr. 22, 2016, Savage et al.
U.S. Appl. No. 15/135,969, filed Apr. 22, 2016, Savage et al.
U.S. Appl. No. 15/135,900, filed Apr. 22, 2016, Savage et al.
Alafort et al., "Lys and Arg in UBI: A specific site for a stable Tc-99m complex?", Nuclear Medicine and Biology 30 (2003) 605-615.
Bakri et al., "Inhibitory effect of garlic extract on oral bacteria", Archives of Oral Biology, 50: 645-651.
Bellini et al., "Cholic and deoxycholic acids derivatives (Part I). Antimicrobial activity of cholane compounds", European J. of Medicinal Chem., 18(2), pp. 185-.
Bellini et al., "Cholic and deoxycholic acids derivatives (Part II). Antimicrobial activity of cholane compounds", European J. of Medicinal Chem., 18(2), pp. 191-195, 1983.
Brown, "Bioisosteres in Medicinal Chemistry, First Edition", edited by Nathan Brown, 2012, Ch. 2 Classical Bioisosteres, pp. 1-52.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
Dörwald, "Side Reactions in Organic Synthesis", 2005, Wiley-VCH Verlag GmbH & Co., KGaA, Weinhelm, Preface. p. IX.
Epand et al., "Bacterial lipid composition and the antimicrobial efficacy of cationic steroid compounds (Ceragenins)", BBA, 2007, pp. 65-78.
Fichna et al., "Synthesis of Target-Specific Radiolabeled Peptides for Diagnostic Imaging", Bioconjugate Chem., 2003, 14, 3-17, American Chemical Society.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lankinen et al., "Ga-Dota-Peptide Targeting VAP-1 for In Vivo Evaluation of Inflammatory and Infectious Bone Conditions", 52nd Annual Meeting of the Orthopaedic Research Society.
Li et al., "Incremental conversion of Outer-Membrane Permeabilizers into Potent Antibiotics for Gram-Negative Bacteria", J. Am. Chem. Soc. 1999, 121, 931-940.
Lowe et al., "Effect of Hydrophobicity of a Drug on its Release from Hydrogels with Different Topological Structures" Journal of Polymer Science (1999) 73: 1031-1039 (9 pages).
Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001 ; 44: No. 1, 20-26).
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Welling et al., "Radiochemical and biological characteristics of 99m-Tc-UBI 29-41 for imaging of bacterial infections", Nuclear Medicine and Biology 29 (2002) 413-422.
Willemen et al., "Micell Formation and Antimicrobial Acivity of Cholic Acid Derivatives with three Permanent Ionic Head Groups", Angew. Chem. Int. Ed., 2002, 41, No. 22.
Williams et al., "In vivo efficacy of a silicone-cationic steroid antimicrobial coating to prevent implant-related infection", Biomaterials, Nov. 2012: 33(33): 8641-8656 (Department of Brigham Young University).
Winter et al., "Improved paragmentic chelate for molecular imaging with MRI", 2005 J. Magn. Magn. Mater. 293: 540-545.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
U.S. Appl. No. 14/624,200, filed Feb. 17, 2015, Office Action dated May 16, 2016.
U.S. Appl. No. 14/602,071, filed Jan. 21, 2015, Office Action dated Aug. 3, 2016.

\* cited by examiner

CSA-136
CLogP: 6.286

CSA-142
CLogP: 5.293

CSA-146
CLogP: 5.822

CSA-137
CLogP: 6.815

CSA-131
CLogP: 7.344

CSA-138
CLogP: 7.873

CSA-134
CLogP: 8.402

CSA-135
CLogP: 9.46

CSA-132
CLogP: 10.518

CSA-133
CLogP: 17.7238

CSA-145
CLogP: 6.88

CSA-144
CLogP: 7.409

HYDROPHOBIC CERAGENIN COMPOUNDS AND DEVICES INCORPORATING SAME

CROSS-REFERENCE TO RELATED APPLICATIONS

This application is a continuation of U.S. patent application Ser. No. 13/554,957, filed Jul. 20, 2012, which claims the benefit of U.S. Prov. App. Nos. 61/572,714 filed Jul. 20, 2011, and entitled "Ceragenin-Containing Hydrogels For Prevention of Bacterial Biofilm Formation," and 61/642,431, filed May 3, 2012, and entitled "Hydrogel Materials Incorporating Eluting Ceragenin Compound," the disclosures of which are incorporated herein in their entirety. This application also claims the benefit of U.S. Prov. App. No. 61/930,580, filed Jan. 23, 2014, and entitled "Cationic Steroidal Antimicrobials," and U.S. Prov. App. No. 61/945,681, filed Feb. 27, 2014, and entitled "Cationic Steroidal Antimicrobial Compounds," the disclosures of which are incorporated herein in their entirety.

BACKGROUND OF THE INVENTION

1. The Field of the Invention

The present invention relates to hydrophobic ceragenin compounds and devices incorporating the hydrophobic ceragenin compounds. The ceragenin compounds have hydrophobic substituents that give the compounds a relatively high C Log P value that allow the compounds to be non-covalently bonded to polymeric materials.

2. The Relevant Technology

Ceragenin compounds, also referred to herein as cationic steroidal anti microbial compounds (CSA), are synthetically produced small molecule chemical compounds that include a sterol backbone having various charged groups (e.g., amine and cationic substituents) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I $NH_2$ $NH_2$ $NH_2$

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

The charged groups are responsible for disrupting the bacterial cellular membrane, and without the charged groups, the ceragenin compound cannot disrupt the membrane to cause cell death or sensitization.

BRIEF SUMMARY

The present invention relates to ceragenin compounds that are relatively hydrophobic despite having a hydrophilic cationic face. The high hydrophobicity has been found to have a surprising and unexpected ability to bond with polymers and then selectively release from the polymeric materials to kill microbes.

In one embodiment, hydrophobic ceragenin compounds disclosed herein have (i) a sterol structure comprising four fused carbon rings; (ii) at least one cationic substituent attached to each of at least three of the four fused carbon rings so as to form an amphiphilic compound having a hydrophobic sterol face and a hydrophilic cationic face; (iii) at least one hydrophobic substituent attached to at least one of the fused carbon rings; and (iv) wherein the CSA compound has a C Log P value of at least 6.0.

The C Log P value is achieved by selecting a proper hydrophobic substituent(s) in combination with proper cationic substituents. The cationic substituents and hydrophobic substituent(s) are selected to give a C Log P value of 6.0 or greater, 6.25 or greater, 6.5 or greater, 7.5 or greater, or even 10 or greater. In order to achieve the desired C Log P value, greater hydrophobicity in the hydrophobic substituent is needed when cationic substituents with less hydrophobicity are used.

The high C Log P value allows the compounds to be non-covalently bonded to polymers that have hydrophobic moieties. For example, the hydrophobic compounds described herein can be non-covalently bonded to a hydrogel materials. The hydrophobic bonding allows for ceragenin compounds to associate with the polymer while having minimal impact on the ability to kill microbes.

Surprisingly and unexpectedly, it has been found that by non-covalently bonding the ceragenin to a polymeric material using hydrophobic/hydrophilic interactions, the hydrophobic ceragenin compound can selectively release from the polymer in the presence of microbes, thereby having a killing affect at lower concentration than one would predict and over an extended period of time. This is in contrast to studies done with covalently bonded ceragenins where immobilization impeded kill rates beyond the initial exposure. The ability of the hydrophobic ceragenin compounds to selectively release from a polymer to kill microbes is highly desirable and a surprising and unexpected result.

In addition, it has been found that the ceragenins as used in the present invention surprisingly kill harmful microbes preferentially over normal flora, which means that the ceragenins can be used at lower concentrations compared to other antimicrobials while achieving the same or better effectiveness. This feature avoids many of the deleterious effects of prior art antimicrobials, many of which tend to kill the "good microbes."

The hydrophobic ceragenin compounds can be incorporated into or formed into medical devices such as medical devices to be implanted into a human or other animal. For example, the hydrogels can be coated on a medical device or incorporated into a polymeric product such as an ophthalmic product. The medical devices incorporating the hydrophobic compounds can controllably release ceragenin compound in a concentration sufficient to meet regulatory requirements for maximum bacterial loads over weeks or even months.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Hydrophobic Ceragenins

Figure 1A:
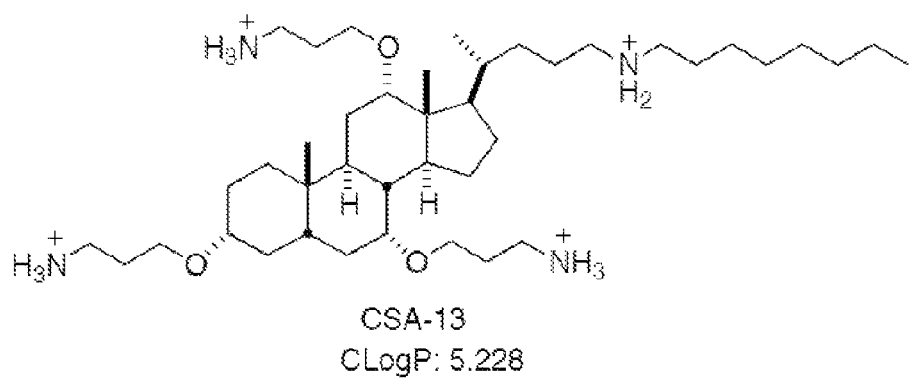
FIG. 1A illustrates example ceragenin compounds with a C Log P value less than 6.5.
Figure 1A:
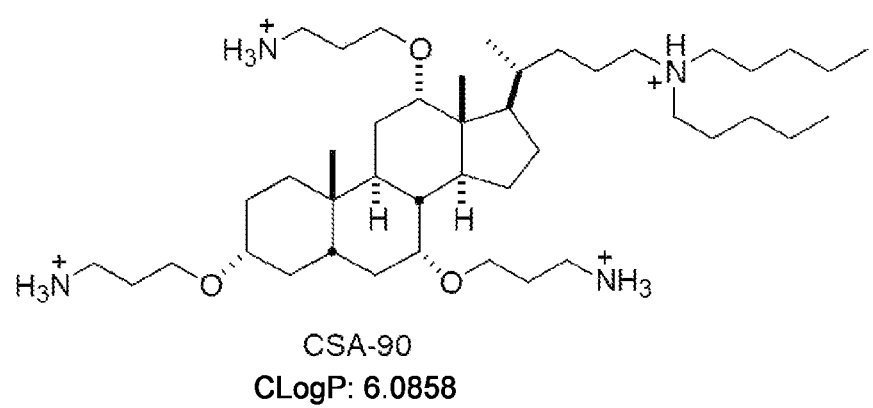
Figure 1A:
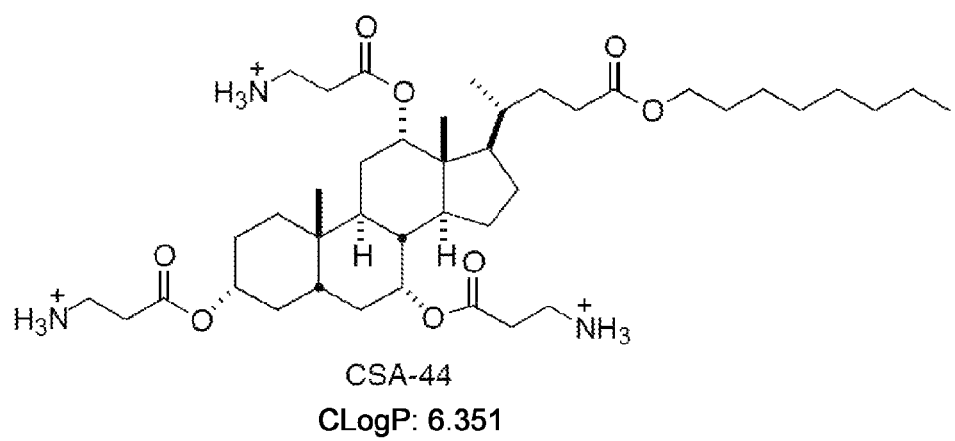
Figure 1A:
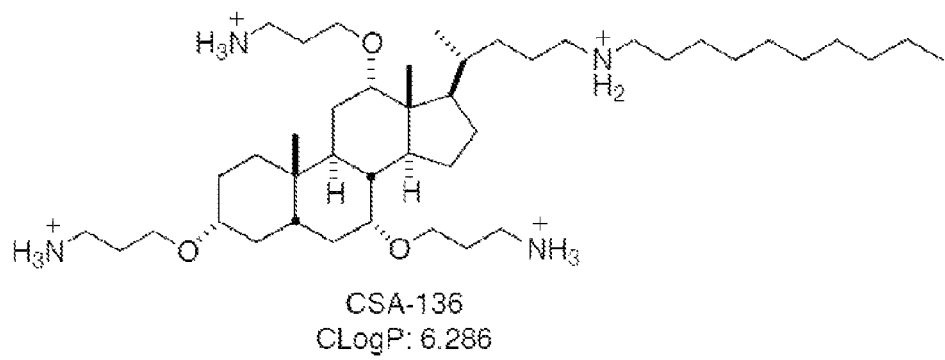
Figure 1A:
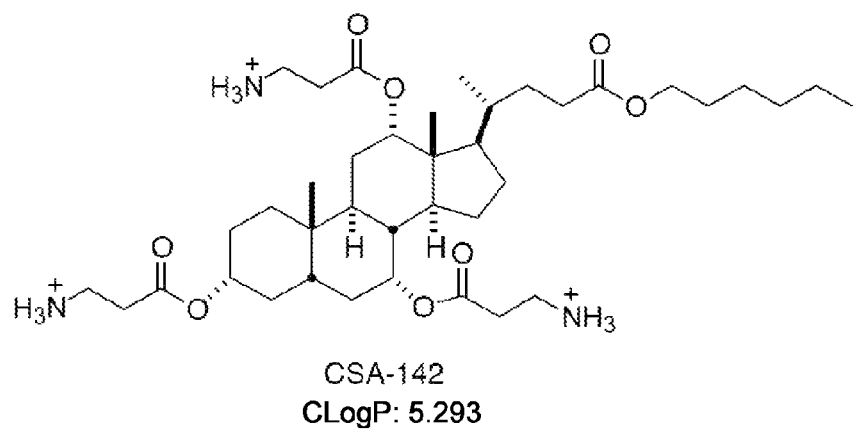
Figure 1A:
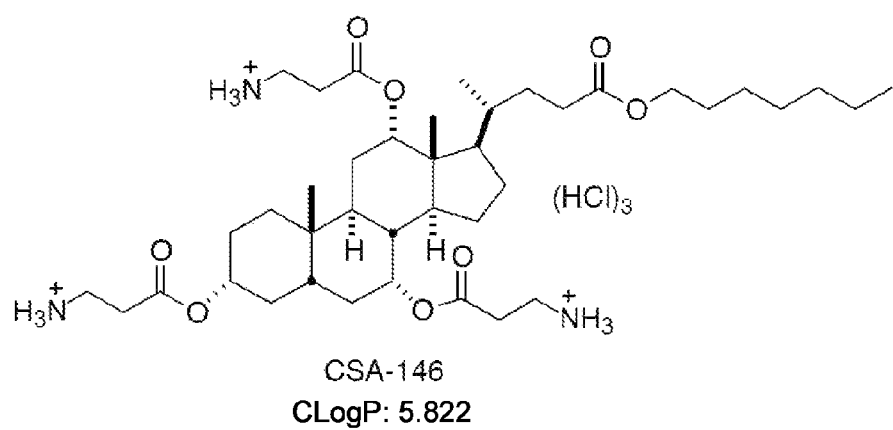

In one embodiment, hydrophobic ceragenin compounds disclosed herein have (i) a sterol structure comprising four fused carbon rings; (ii) at least one cationic substituent attached to each of at least three of the four fused carbon rings so as to form an amphiphilic compound having a hydrophobic sterol face and a hydrophilic cationic face; (iii) at least one hydrophobic substituent attached to at least one of the fused carbon rings; and (iv) wherein the CSA compound has a C Log P value of at least 6.0, at least 6.25, at least 6.5, at least 7.5, or at least 10.

The C Log P value is achieved by selecting a proper hydrophobic substituent(s) in combination with proper cationic substituents. The cationic substituents and hydrophobic substituent(s) are selected to give a C Log P value of 6.0 or greater, 6.25 or greater, 6.5 or greater, 7.5 or greater, or even 10 or greater.

The ceragenin compound may have a structure as shown in Formula I:

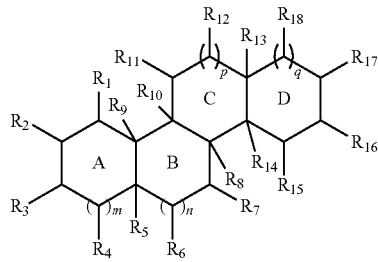

Formula I

Where:
rings A, B, C, and D form a fused ring system and at least one of the R groups on 2 or 3 of the 4 four fused rings has a cationic substituent. The other R groups on Figure I can have a variety of different functionalities, thus providing the ceragenin compound with the desired hydrophobic properties.

In a preferred embodiment, p=1 and q=0 and at least $R_3$, $R_7$, and $R_{12}$ independently include a cationic substituent attached to the fused ring system and $R_{17}$ is a hydrophobic substituent that includes a hydrophobic group selected to give the ceragenin compound its desired hydrophobic/hydrophilic characteristics, which allows the ceragenin compound to non-covalently bond to a polymer and elute out over time and/or be selectively exposed to microbes. The $R_{17}$ substituent may be hydrophobic but still include one or more heteroatoms (O or N) by having sufficient number of carbon atoms attached thereto to form a hydrophobic group. The hydrophobic group may be branched, substituted, or unsubstituted and the branching may occur at the heteroatom (e.g., dialkyl amines). The hydrophobic substituent is preferably attached at $R_{17}$ when q=0 and $R_{18}$ when q=1, but may be attached at other locations on the D ring or on R groups at locations on rings A, B, or C of Formula I. Where a hydrophobic substituent has a hydrophobic group attached to a heteroatom of an alkyl group, the hydrophobic group may have from 1-20 carbons, preferably 8, 9, 10, 11, 12, 13, 14, 15 or more carbons and 20, 18, 17, 16, 15 or fewer carbons or within a range thereof. The hydrophobic group may also include a hydrophobic moiety such as trimethylsilane. The hydrophobic group may include one or more alkyl groups each having 4 or more, 6 or more, 8 or more, 10 or more or 12 or more carbons. The hydrophobic group can be attached to the sterol structure by an alkyl group linking to the heteroatom. The linkage may be an ester, an ether, an amine, or an amide. Ester linkages are preferred where hydrolysis is desired and/or no charge is desired to impart greater hydrophobicity. There the heteroatom includes an amine, the hydrophobic group is preferably a dialkyl. Examples of a suitable hydrophobic substituents having a hydrophobic group as described herein are $C_{13}$-alkylamino-$C_5$-alkyl and di-$(C_1$-$C_{20})$ alkylamino-$(C_1$-$C_{10})$-alkyl, which can be covalently bonded to the D ring at $R_{17}$ or $R_{18}$ (Formula I).

Figure 1B:
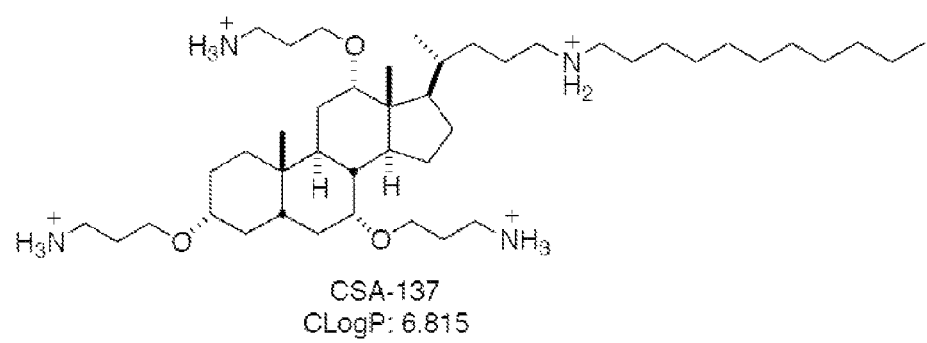
FIG. 1B illustrates example ceragenin compounds with a C Log P value greater than 6.5.
Figure 1B:
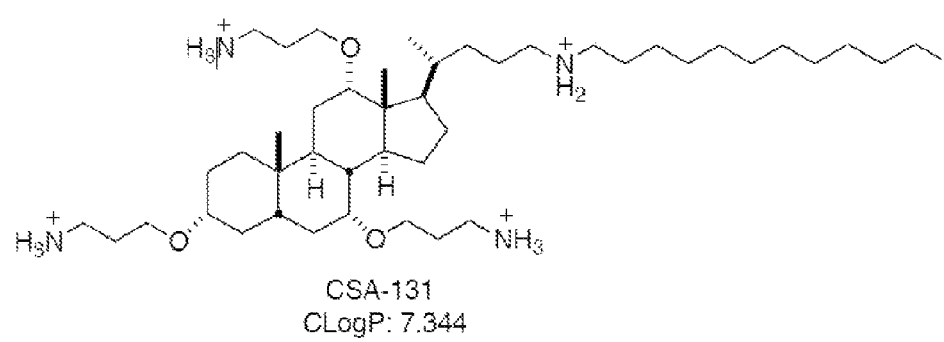
Figure 1B:
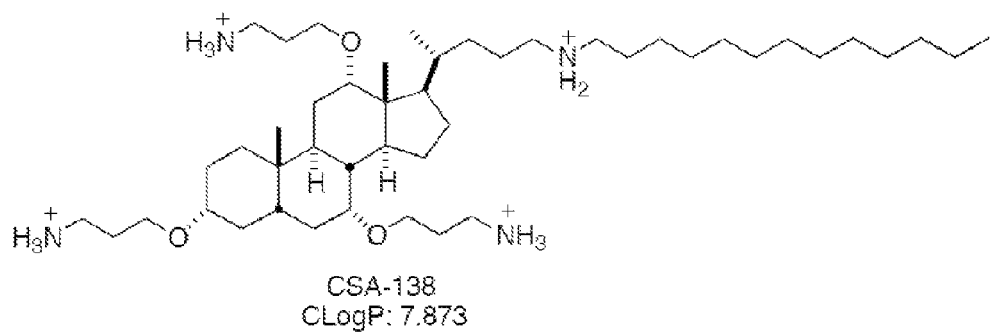
Figure 1B:
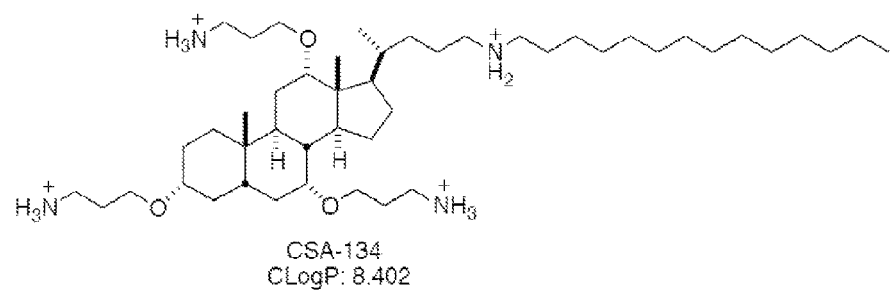
Figure 1B:
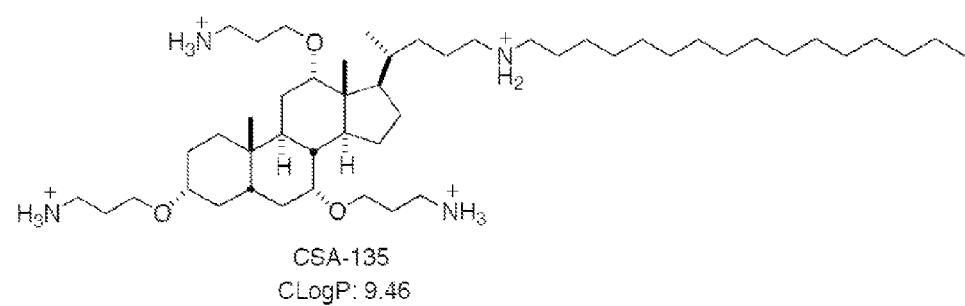
Figure 1B:
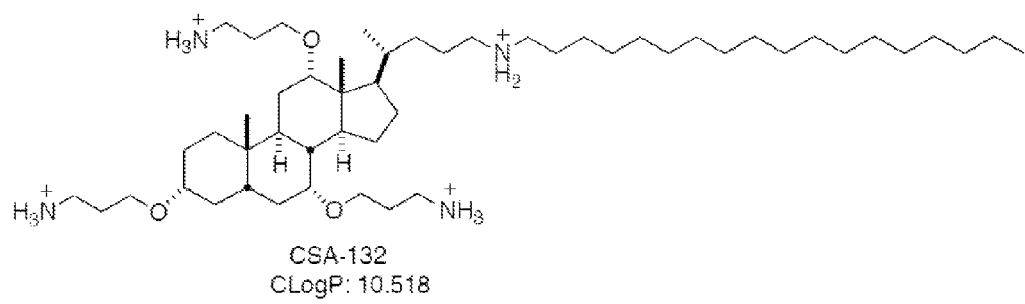
Figure 1B:
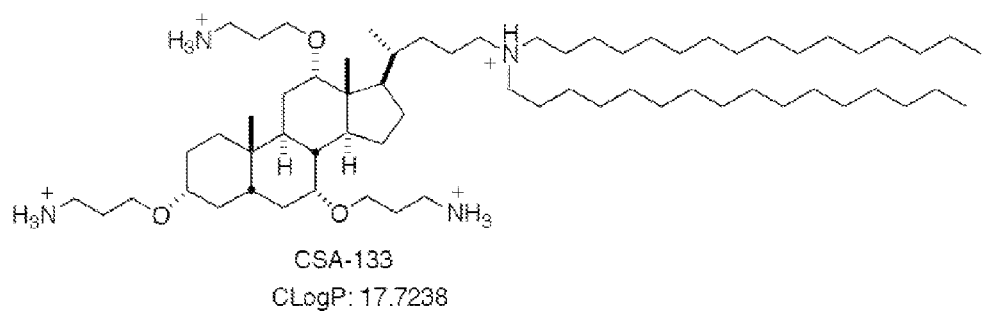
Figure 1B:
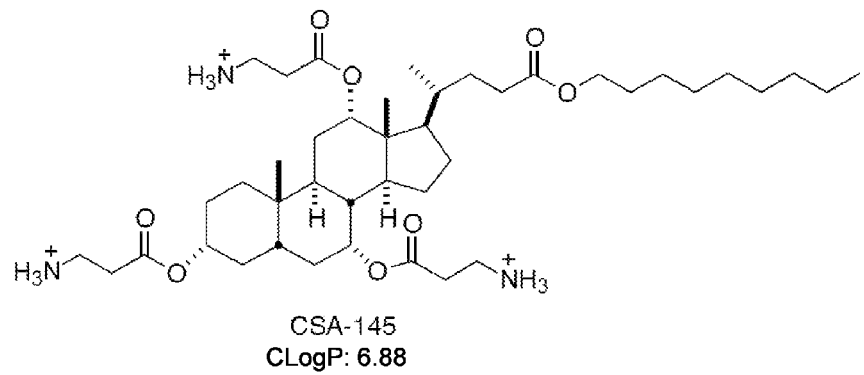
Figure 1B:
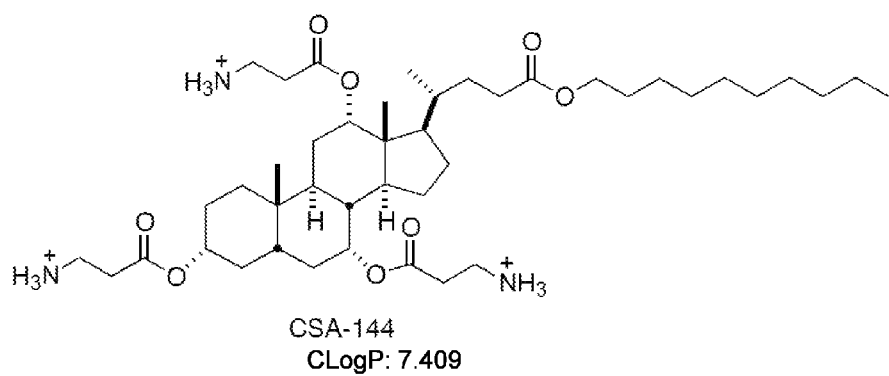
Figure 1B:
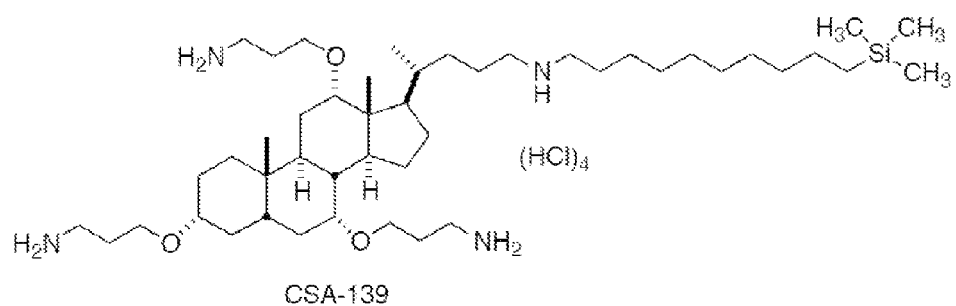

A number of examples of compounds of Formula I that may be used in the embodiments described herein are illustrated in FIG. 1B. Suitable examples of hydrophobic ceragenins useful in producing a composition that will selectively elute from a polymer include, but are not limited to, CSA-131, CSA-132, CSA-133, CSA-134, CSA-135, CSA-137, CSA-138, CSA-144, and CSA-145. The foregoing compounds have a C Log P value greater than 6.5, 7.5, 8.5, and in some cases greater than 10. Nevertheless, CSA- 135 was found to be less satisfactory compared to other ceragenins disclosed herein having different C Log P values relative to their ability to elute and kill microbes in a desired manner. For example, CSA-136 was unexpectedly found to be advantageous over CSA-135 in its ability to elute and kill microbes. This suggests that desirable C Log P values between 6.0 and 9.0 may be desirable in some cases.

FIG. 1A illustrates compounds that have a C Log P value less than 6.5. When contrasted with the compounds of FIG. 1B, the compounds of FIG. 1A illustrate the types of changes that impart hydrophobicity of a C Log P value greater than 6.0, 6.25, 6.5, 7.5, 8.5, or 10. For example, where the heteroatom is part of an ester group, a hydrocarbon chain length of 9 or greater extending beyond the heteroatom is sufficient to impart the desired hydrophobicity. Where an amine group is the heteroatom, a hydrocarbon chain length of 11 carbon atoms or greater extending beyond the heteroatom is sufficient to impart a C Log P value greater than 6.5 (with the proviso that CSA-135 was unexpectedly found to be less satisfactory than CSA-136 in its ability to elute and kill microbes). Other moieties such as trimethyl silane can be added to allow for amine groups to be used with shorter chain lengths or to provide additional hydrophobicity.

With reference again to Formula I, more specifically, each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, and $R_{16}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$)alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(O)—O—, $H_2N$—HC($Q_5$-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and ($C_1$-$C_{10}$) guanidinoalkylcarboxy, where $Q_5$ is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino ($C_1$-$C_{10}$) alkylamino, a substituted or unsubstituted ($C_1$-$C_{10}$) aminoalkylcarboxy, a substituted or unsubstituted arylamino ($C_1$-$C_{10}$) alkyl, a substituted or unsubstituted ($C_1$-$C_{10}$) aminoalkyloxy ($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_{10}$) aminoalkylcarboxyamido, a ($C_1$-$C_{10}$) quaternaryammonium alkylcarboxy, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and a ($C_1$-$C_{10}$) guanidinoalkylcarboxy; or a pharmaceutically acceptable salt thereof. Additional examples of specific CSA compounds are disclosed in Applicant's copending U.S. application Ser. No. 13/288,902 Filed Nov. 3, 2012, which is incorporated herein by reference.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —$CH_2$—(C=O)—$NH_2$ (asparagine), —$CH_2$—SH (cysteine), and —CH(OH)—$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyan, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyan, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_6$-$C_{14}$, $C_{6-10}$ aryl groups).

Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is ($C_1$-$C_{10}$) alkyloxy-($C_1$-$C_{10}$) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, Protective Groups in Organic Chemistry, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all β-substituted or α-substituted. The configuration of the moieties $R_3$, $R_7$ and $R_{12}$ may be important for interaction with the cellular membrane.

Compounds include but are not limited to compounds having cationic substituents (e.g., amine or guanidine groups) covalently attached to a sterol backbone or scaffold at any carbon position, e.g., cholic acid. In various embodiments, a group is covalently attached at any one or more of positions $R_3$, $R_7$, and $R_{12}$ of the sterol backbone. In additional embodiments, a group is absent from anyone, or more, of positions $R_3$, $R_7$, and $R_{12}$ of the sterol backbone.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

Ceragenins with hydrophobic substituents can be prepared using the techniques described in Applicant's U.S. Pat. No. 6,767,904, with the modification being using longer chain alkyls to form a more hydrophobic substituent. For example, instead of using an octyl amine to form the functional group at $R_{17}$, a corresponding longer chain amine can be used.

II. Non-Covalent Incorporation of Ceragenins into a Polymer

Hydrophobic ceragenin compounds incorporated into a polymer can be non-covalently associated with the polymer. Upon contact with moisture, the ceragenin can leach or elute from the polymer. Ceragenins are generally soluble in water, and ceragenins can be associated with polymers to control release rates. Selection of appropriate polymer and ceragenin structures allows for an extended period of release of the ceragenin.

For example, the chain extending from a heteroatom (e.g., N) on $R_{17}$ (Formula I) can be tailored to allow varied rates of elution from a hydrogel polymer. Exemplary chains included, lipids, hydrophobic chains (e.g., aliphatic), hydrophilic (e.g., polyethyleneoxide), or any chain that interacts with the polymer is a way that allows modification of the rate of elution. Longer chain lengths will retain the ceragenin within the polymer matrix (in particular the hydrophobic domains). In one embodiment, the ceragenin compound may have a carbon chain of at least 9 carbons attached to the D ring of the sterol group (Formula I). For example, the carbon chain of at least 9 carbons may be attached to $R_{17}$ group of Formula I, or the $C_{24}$ carbon or other similar carbon of a sterol backbone.

The particular ceragenins incorporated into the polymer may be soluble or partially soluble in aqueous solutions. Additionally, ceragenins when blended with the water and the appropriate surfactant can be handled in the form of gels, or emulsions. Block copolymers based on ethylene oxide and/or propylene oxide, in particular, Pluronic-type surfactants, are especially useful for this purpose. Pluronic is a product of BASF, a business with offices in Port Arthur, Tex., USA.

Ceragenin compounds can be incorporated into a polymer at any suitable step during manufacture of a hydrogel material or product. For example, in an embodiment, a polymer can be brought into contact with a solution of ceragenins by immersion, spraying, printing, or coating, etc. Suitable solvents include short chain alcohols such as ethanol, methanol, isopropyl alcohol, and the like. If desired, the solvent used to incorporate the ceragenin can be removed, for example, by evaporation. If necessary the polymer can be dried by utilizing forced hot air, oven drying, air at room temperature, microwave drying, or the use of heated drying drums, vacuum chambers, etc. In some manufacturing systems the normal air flow and temperature sufficiently dry the substrate without a discrete drying process.

Ceragenin compounds are known to be soluble in water. Alternatively, ceragenin compounds are also soluble in such materials as ethanol (and other alcohols), propylene glycol, glycerine, and polyols, or mixtures thereof with or without water can be used in incorporate ceragenin compounds into a polymeric material. Furthermore ceragenins can be incorporated as gels, emulsions, suspensions, and in dry form.

In another embodiment ceragenin is incorporated into a polymer during polymerization of the monomers. In these processes, the ceragenin can be included in the monomer blend during polymerization. The ceragenin in final polymer can be noncovalently incorporated into the polymer and will accordingly elute when contacted with a solvent such as water.

III. Elution

When the ceragenin compound is incorporated into a polymeric material, the hydrophobicity/hydrophilicity of the polymer and the ceragenin compound are selected to cause the ceragenin compound to non-covalently bond to the hydrogel polymer. The non-covalent bonding prevents the ceragenin compound from being released all at once in the presence of a solvent. Rather, the bonding allows the ceragenin compound to be released over time in the presence of a solvent.

The non-covalent bonding depends on the composition of both the polymer and the ceragenin and therefore need to be selected together to produce the desired elution. The selection is typically carried out by selecting a particular polymer having desired chemical and mechanical properties for a particular application. For example, if the polymer is coated on a medical device to be implanted in vascular tissue, the polymer is selected for compatibility with vascular tissue and blood. If the polymer is used to form a contact lens, the polymer is selected for its compatibility with the eye and the need to form the polymer in a shape that will correct vision. The hydrophobicity/hydrophilicity of the polymer material is therefore somewhat constrained by the particular application.

The ceragenin compound has a hydrophobicity selected to provide non-covalent bonding to the particular polymer. The ceragenin may be selected to have R groups that bond non-covalently the functional groups of the polymer. For example, a polyacrylate based polymer may have a certain percentage of hydrophobic groups and hydrophilic groups in the polymer matrix and the ceragenin compound may be selected to have a hydrophobic $R_{17}$ substituent (where q=0 in Formula I) that non-covalently bonds to the hydrophobic groups of the polymer to cause a relatively consistent elution over a period of days or weeks.

In some cases, the solvent may also influence elution. In one embodiment, the solvent is water. In some embodiments, the solvent may be saline.

In one embodiment, the hydrogel polymer and the ceragenin compound are selected to yield non-covalent bonding that provides a release rate of 0.1-100 µg/ml, 0.5-50 µg/ml, or 1-10 µg/ml at three days, one week, or one month in water or saline. In one embodiment, the foregoing elution rate remains within the foregoing ranges for at least 3 days, one week, or one month. These elution rates are achieved in part by the non-covalent bonding that prevents rapid release of the compound, which results in more compound being available at a later date.

As mentioned above, it has been surprisingly found that non-covalently bound ceragenins in hydrogels selectively elute in the presence of microbes. This is a surprising and unexpected result that makes the use of polymer-ceragenin compounds particularly advantageous as compared to other materials, such as ceragenins covalently bonded to the surface of a polymer.

Those skilled in the art will recognize that the selection of the particular polymer and ceragenin compound will depend on the particular application and the appropriate selection can be made by one of skill in the art using the teachings and examples provided herein.

IV. Hydrogel Polymers

One type of polymer that is particularly useful for incorporating hydrophobic ceragenin compounds are hydrogel polymers.

Examples of suitable hydrogel polymers include, but are not limited to, polyvinyl alcohol, sodium polyacrylate, acrylate polymers, polyethylene oxide, poly(2-acrylamido-2-methyl-1-propanesulfonic acid) (polyAMP S), polyvinylpyrrolidone, polyacrylamide, silicone, agarose, methylcellulose, hyaluronan, hydrolyzed polyacrylicnitrile, combinations of these. The hydrogels may be copolymers. The copolymers may include hydrophobic and hydrophilic units.

In one embodiment, the hydrogel is suitable for manufacturing a contact lens. Hydrophilic contact lenses can be formed from cross-linked polymers based on hydrophilic derivatives of acrylic or methacrylic acid, hydrophilic vinylic monomers such as vinylpyrrolidone, and the like. The hydrogels preferably include hydrophobic regions made from blocks or monomers that are hydrophobic.

An example of a suitable contact lens hydrogel is disclosed in U.S. Pat. No. 8,011,784, which is incorporated herein by reference.

The hydrogel polymers may be formed into a contact lens having a shape and structure suitable for correcting vision. Those skilled in the art are familiar with the shapes and structures of hydrogel polymers that can provide correction for vision. Other devices that can be formed from the hydrogels include wound healing devices such as tissue scaffolds and wound dressing.

V. Medical Devices and Coatings

Figure 2:
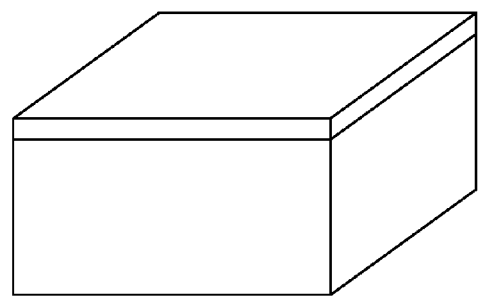
FIG. 2 is a schematic representation of a substrate with a polymeric coating.

The polymers described herein may be used in various applications, including, but not limited to, medical devices, coatings, bandages, implants, tissue scaffolding, and the like. FIG. 2 is a schematic representation of a medical device 100 that includes a substrate 110 and a polymeric coating 120.

The substrate 110 may be made of any material suitable for supporting and/or adhering to a hydrogel material. The substrate can be polymeric, metallic, an alloy, inorganic, and/or organic. In one embodiment, the substrate is a biocompatible or bioabsorbable material. Suitable biocompatible metallic materials include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and the like, and combinations of these)

The thickness of the substrate will depend on the device and the material but may be 0.1, 1.0, 10 mm or greater and/or 100, 10, or 1 mm or less and/or within a range thereof.

The thickness of polymeric coating 120 is generally less than the thickness of substrate 110. Polymeric coating 120 may have a thickness of 0.01, 0.1, 1.0, or 10 mm or greater and 100, 10, 1.0, or 0.1 mm or less or within a range thereof.

The polymeric coating 120 can be continuous or non-continuous. The coating may be applied to the substrate using techniques such as dip coating, spin coating, or the like.

Examples of medical devices that can be formed from a polymer containing hydrophobic ceragenin compounds or can have such a polymer coated thereon include but are not limited to bone implants, bone pins, bone screws, tissue grafts, airway devices such as endotracheal tubes, implantable devices such as coronary stents, peripheral stents, catheters, arterio-venous grafts, by-pass grafts, pacemaker and defibrillator leads, anastomotic clips, arterial closure devices, patent foramen ovale closure devices, and drug delivery balloons. The polymer may be coated on or form any portion of the structures of such devices and is preferably on an outer surface and more preferably on an out service that contacts tissue or a tissue air interface (when the device is implanted).

VI. Stabilization of Ceragenins by pH

In one embodiment a ceragenin compound can have hydrolysable linkages that attach the cationic substituents to the sterol group (e.g., ester bonds). Hydrolysis of these linkages inactivates the ceragenin. To make the ceragenin stable, an acid can be added to achieve a pH less than 6, 5.5, 5, or 4.5 and optionally greater than 2, 2.5, or 3 or a range thereof. Stability before use is important to give a desired shelf life and instability during and after use can be desirable to prevent long term accumulation of ceragenins in biological systems.

It may be advantageous to adjust the degree of neutralization of the polymer to improve the stability of the ceragenin. The degree of neutralization of the polymer can be adjusted during its manufacturing process, or subsequently. Alternatively, the ceragenin can be suspended or dissolved in an acidic solution; and when the ceragenin suspension or solution is added to the hydrogel polymer the degree of neutralization of the hydrogel would thereby be adjusted.

VII. Examples

To better understand the mechanism by which hydrophobic ceragenin compounds can prevent bacterial colonization, the bonding between CSA-138 and a hydrogel used in contact lenses was evaluated. In a first example, we determined the rate at which CSA-138 elutes from a hydrogel suitable for use in contact lenses. To quantify the amount of ceragenin eluting from the hydrogel, we used LC/MS using a mass-labeled internal standard. However, this method only gave detection limits of about 2 µg/ml, and we were able to effectively kill bacteria at constant elution rates below the detection limit. For example, the elution fell below detection limits within five days of elution from lenses in which CSA-138 had been incorporated at 1%, yet the ceragenins appeared to still be providing suitable kill rates.

To decrease the detection limit for CSA-138, we prepared a radiolabeled version of CSA-138 (CSA-138T2), incorporated it into contact lenses, and quantified its elution from lenses using scintillation counting.

Example 1

Lenses containing 1% CSA-138 were stored in 0.5 mL phosphate buffered saline (PBS) prior to testing. One set of lenses was autoclaved for 45 min before elution studies were performed. For elution studies, lenses were suspended in 2 ml aliquots of PBS, 10% TSB growth medium, 10% TSB growth medium containing $10^6$ CFU of Staphylococcus aureus, or 10% TSB growth medium containing $10^6$ CFU of Pseudomonas aeruginosa. Corresponding aliquots were exchanged every 24 h, including bacterial inocula. Samples were removed every 24 h and analyzed for the presence of CSA-138 using scintillation counting. A standard curve was generated to correlate counts per minute to concentration of CSA-138. All experiments were performed in triplicate.

Figure 3:
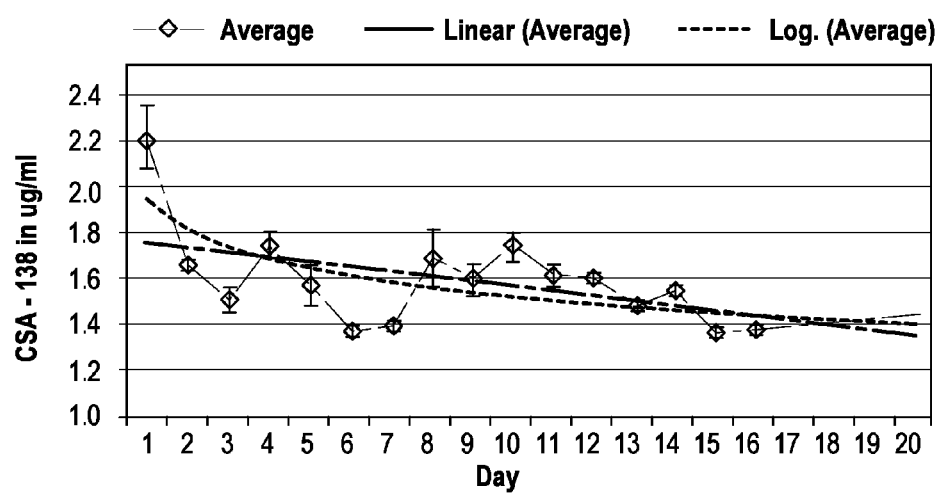
FIG. 3 is a graph showing elution of a ceragenin from a hydrogel in phosphate buffered saline.

Though some variations from day to day were observed, a recognizable trend was observed in the elution profile of lenses suspended in PBS (FIG. 3). As expected, the elution on the first day was relatively high (about 2.2 µg/ml). Over the course of following 19 days, daily elution changed from approximately 1.6 to 1.4 µg/ml per day.

Figure 4:
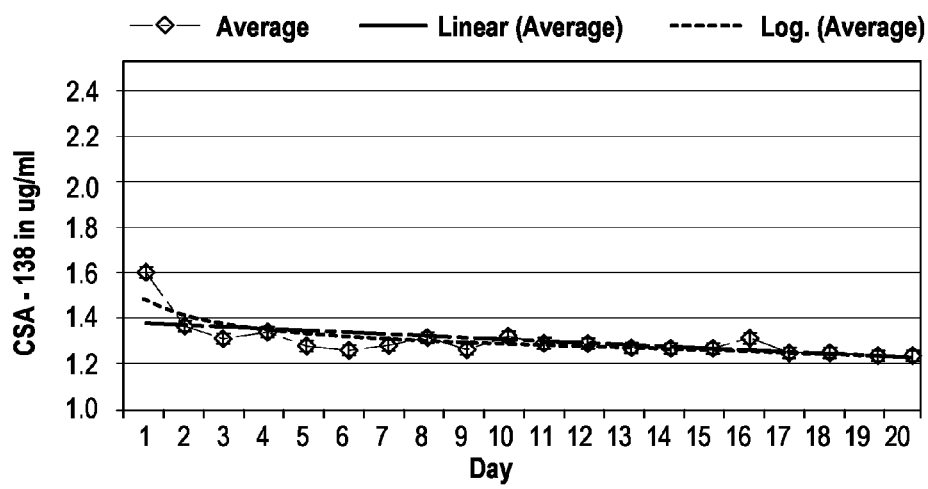
FIG. 4 is a graph showing elution of a ceragenin from a hydrogel following autoclaving.

A comparable elution profile was observed with lenses that were autoclaved prior to the start of the study, except that the initial amount of material that eluted decreased somewhat (FIG. 4). This decrease in elution is likely due to enhanced elution into the storage solution during the autoclaving process. Over the course of the study (from day 2 to 20), the amount of CSA-138 that eluted changed from approximately 1.4 to 1.2 µg/ml per day.

It was anticipated that an increase in the osmolality of an aqueous solution would decrease the solubility of CSA-13 and slow elution. We determined the elution profile in 10% TSB in PBS, and as expected elution decreased (FIG. 5) to match that seen with lenses that had been autoclaved.

Figure 6:
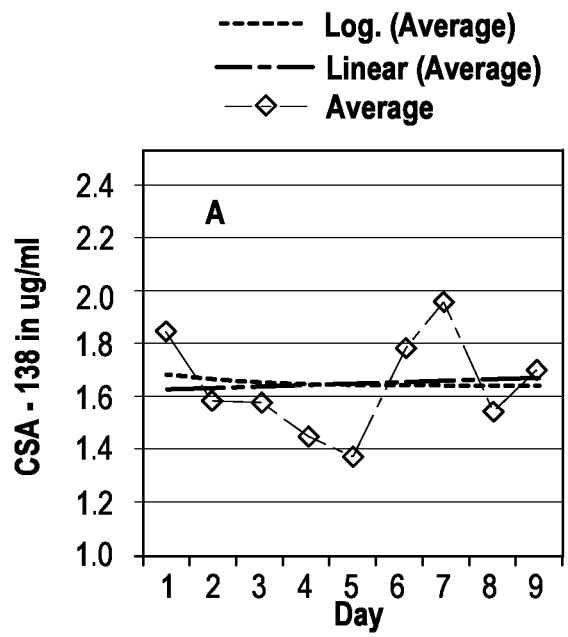
FIG. 6 is a graph showing elution of a ceragenin from a hydrogel in buffer and $10^6$ CFU of S. aureus.
Figure 7:
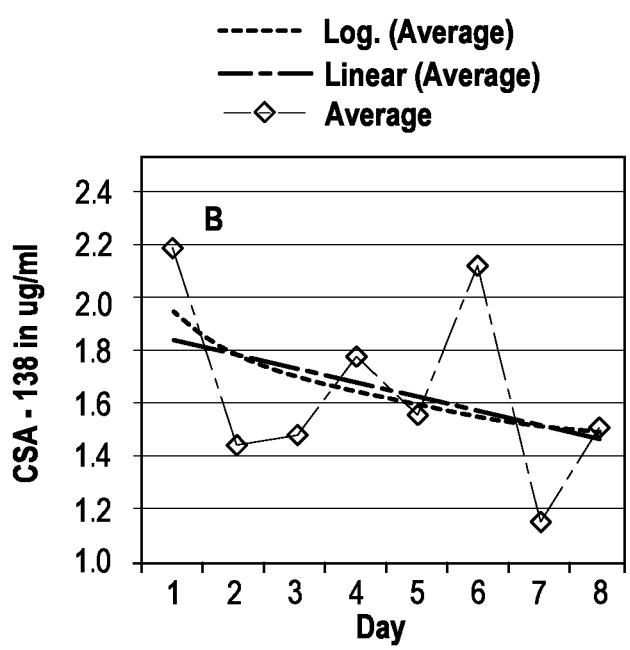
FIG. 7 is a graph showing elution of a ceragenin from a hydrogel in buffer and $10^6$ CFU of P. aeruginosa.
Figure 2:
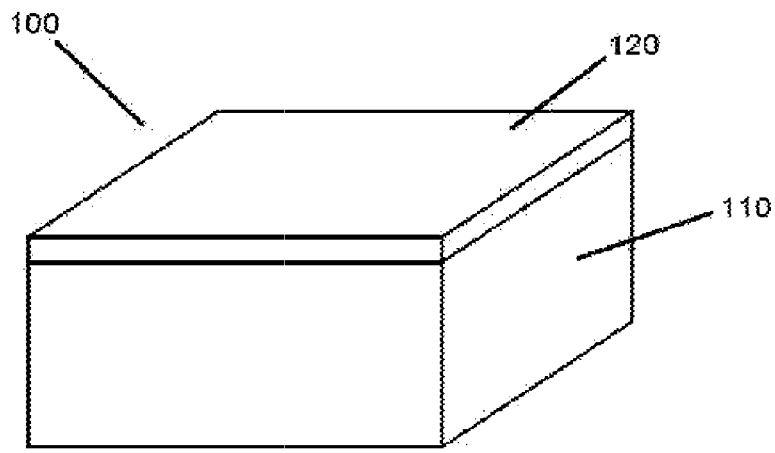

Because kill rates appeared to be happening at such low concentrations, we hypothesized that the presence of bacteria was influencing the elution of CSA-138 from lenses. To test this hypothesis, lenses were incubated with S. aureus or P. aeruginosa and elution was monitored. These experiments were performed for nine and eight days, respectively. Elution of CSA-138 fluctuated substantially and to a much greater extent than outside of the presence of bacteria (FIGS. 6 and 7). Because of these variations, the experiments were shortened relative to elution experiments without bacteria. Though there was substantial variation in the elution in the presence of bacteria, it was possible to determine the significance of the differences in elution comparing samples with and without bacteria. After the first day, differences gave a p value of 0.05 and for many of the days, the p value was below 0.01. These results argue that bacteria impact elution of CSA-138 from lenses.

The MIC values of CSA-138 for S. aureus and for P. aeruginosa are 0.5 and 1.0 µg/ml, respectively. The elution of CSA-138 from lenses gives concentrations that are just able to eliminate the inocula introduced. Autoclaving the lenses, increasing the osmolality in the surrounding solution, and the presence of bacteria impact the elution profile modestly.

Figure 5:
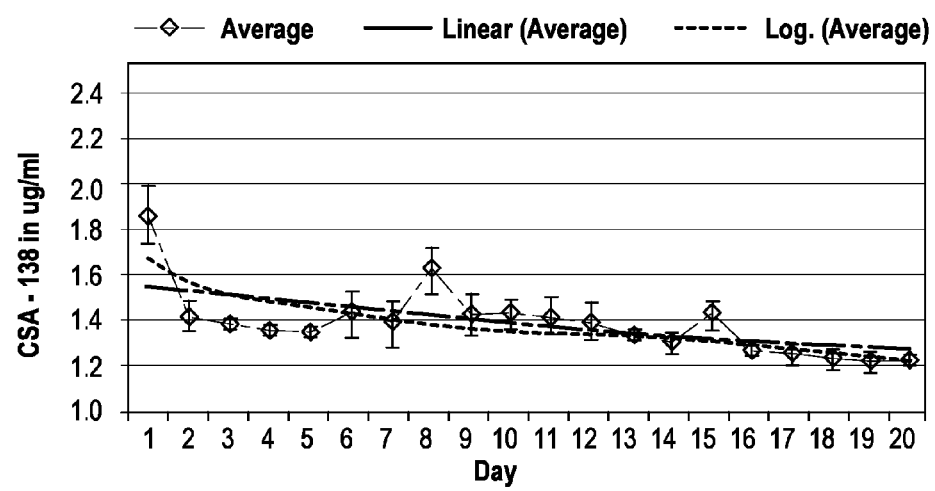
FIG. 5 is a graph showing elution of a ceragenin from a hydrogel in phosphate buffered saline and tryptic soy broth.

If one takes the elution profile given in FIG. 5 and extends the trend until elution of CSA-138 drops below 1 µg/ml, this would require about 40 days (elution decreases from 1.4 to 1.2 µg/ml per day between days two and 20; a decrease from 1.2 to 1.0 µg/ml per day would be expected to require another 19 days). Thus, it would be expected that elution of CSA-138 would be sufficient to eliminate reasonable inocula of bacteria for as many as 40 days. As noted in a previous report, elution of CSA-138 from lenses prevents colonization by S. aureus for 30 consecutive days and by P. aeruginosa for 19 days. These studies are performed with relatively high inocula ($10^6$ CFU), and it is anticipated that CSA-138 eluting after 30 days would be sufficient to eliminate smaller inocula.

Optimization of the structure of CSA-138 has yielded a potent antimicrobial agent that associates with contact lens material and elutes at the concentration necessary to eliminate substantial inocula of Gram-positive and -negative bacteria. Considering the number of bacteria to which lenses are typically exposed, it is likely that lower concentrations of CSA-138 could be used while continuing to prevent bacterial growth on lenses.

For purposes of this invention, "physiological conditions" are aqueous conditions where the pH, temperature, and salt concentrations are generally suitable for sustaining life (e.g., for many, but not all devices, physiological conditions is often a pH near 7, temperatures near 37° C., and salt concentration near 150 mM).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hydrophobic cationic steroidal anti-microbial (CSA) compound comprising:
a sterol structure comprising four fused carbon rings;
at least one cationic substituent attached to each of at least three of the four fused carbon rings so as to form an amphiphilic compound having a hydrophobic sterol face and a hydrophilic cationic face; and
at least one hydrophobic substituent attached to at least one of the fused carbon rings;
wherein the CSA compound has a structure as in Formula I:

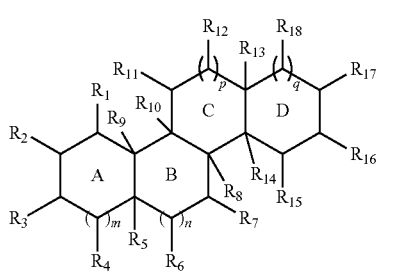

Formula I where
q=0 such that $R_{18}$ is omitted, m and n are independently 0 or 1, and p=1;
two or three of $R_3$, $R_7$, and $R_{12}$ independently include a cationic group;
$R_1$-$R_4$, $R_6$, $R_7$, $R_{11}$, $R_{12}$, $R_{15}$, and $R_{16}$ are independently selected from the group consisting of hydrogen, hydroxyl, substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$)alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, substituted or unsubstituted ($C_1$-$C_{10}$) aminoalkyl, substituted or unsubstituted aryl, substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, linking group attached to a second steroid, substituted or unsubstituted ($C_1$-$C_{10}$) aminoalkyloxy, substituted or unsubstituted ($C_1$-$C_{10}$) aminoalkyloxy-($C_1$-$C_{10}$) alkyl, substituted or unsubstituted ($C_1$-$C_{10}$) aminoalkylcarboxy, substituted or unsubstituted ($C_1$-$C_{10}$) aminoalkylaminocarbonyl, substituted or unsubstituted ($C_1$-$C_{10}$) aminoalkylcarboxamido, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternary ammonium alkylcarboxy, and ($C_1$-$C_{10}$) guanidinoalkyl carboxy, where $Q_5$ is a side chain of an amino acid, and P.G. is an amino protecting group;

$R_5$, $R_8$-$R_{10}$, $R_{13}$, and $R_{14}$ are independently deleted when one or more of fused rings A, B, C, or D is unsaturated so as to complete the valency of the carbon atom at that site or, when fused rings A, B, C, and D are saturated, are independently selected from the group consisting of hydrogen, hydroxyl, substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, substituted or unsubstituted ($C_1$-$C_{10}$) aminoalkyl, substituted or unsubstituted aryl, ($C_1$-$C_{10}$) haloalkyl, $C_2$-$C_6$ alkenyl, $C_2$-$C_6$ alkynyl, oxo, linking group attached to a second steroid, substituted or unsubstituted ($C_1$-$C_{10}$) aminoalkyloxy, substituted or unsubstituted ($C_1$-$C_{10}$) aminoalkylcarboxy, substituted or unsubstituted ($C_1$-$C_{10}$) aminoalkylaminocarbonyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and ($C_1$-$C_{10}$) guanidinoalkylcarboxy, where $Q_5$ is a side chain of an amino acid and PG. is an amino protecting group; and $R_{17}$ is a hydrophobic substituent which includes a heteroatom and at least one hydrocarbon group comprising a carbon chain of at least 9 carbon atoms distal to the heteroatom, with the proviso that $R_{16}$ does not form a fused ring with $R_{17}$ and $R_{17}$ does not include a total of 16 carbon atoms distal to the heteroatom.

2. The hydrophobic CSA compound as in claim 1, wherein the C Log P value is at least 6.5.

3. The hydrophobic CSA compound as in claim 1, wherein the C Log P value is at least 10.

4. The hydrophobic CSA compound as in claim 1, wherein the C Log P value is between 6.0 and 9.0.

5. The hydrophobic CSA compound as in claim 1, wherein the at least one hydrophobic substituent includes a trimethylsilane.

6. The hydrophobic CSA compound as in claim 1, wherein the at least one hydrocarbon group comprises a straight chain hydrocarbon.

7. The hydrophobic CSA compound as in claim 1, wherein the at least one hydrocarbon group distal to the heteroatom of $R_{17}$ has 9-15 carbon atoms.

8. The hydrophobic CSA compound as in claim 1, wherein the at least one hydrocarbon group distal to the heteroatom of $R_{17}$ comprises a carbon chain of at least 11 carbon atoms, with the proviso that the carbon chain does not contain 16 carbon atoms.

9. The hydrophobic CSA compound as in claim 1, wherein the at least one hydrocarbon group distal to the heteroatom of $R_{17}$ comprises at least 17 carbon atoms.

10. The hydrophobic CSA compound as in claim 1, wherein the CSA compound of Formula I is selected from the group consisting of:

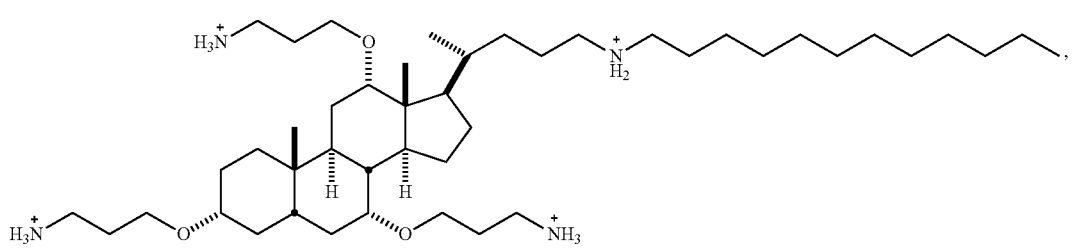

CSA-131

-continued
CSA-132
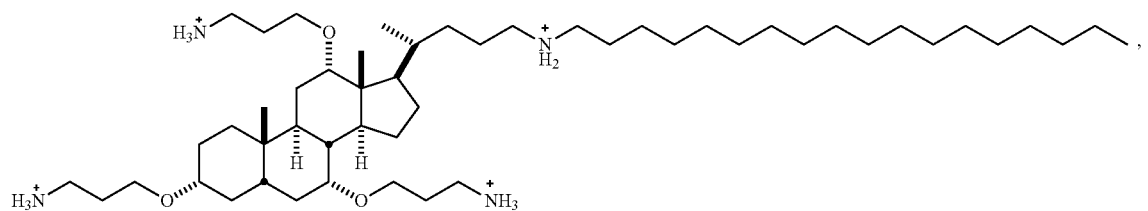
CSA-133
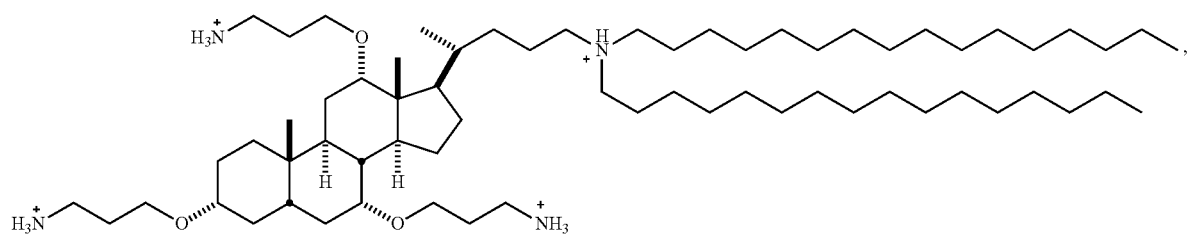
CSA-134
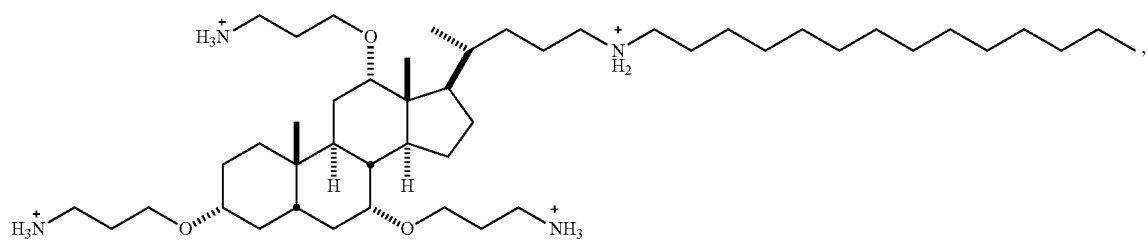
CSA-136
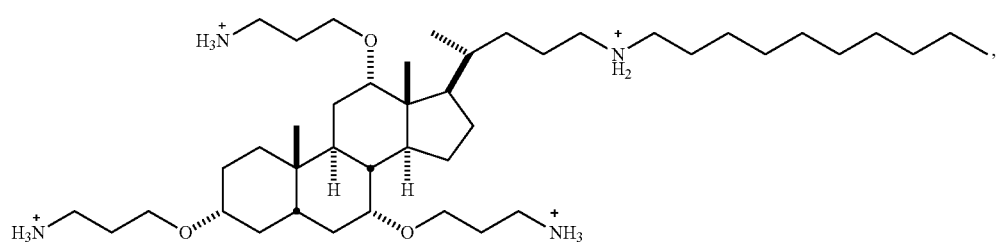
CSA-137
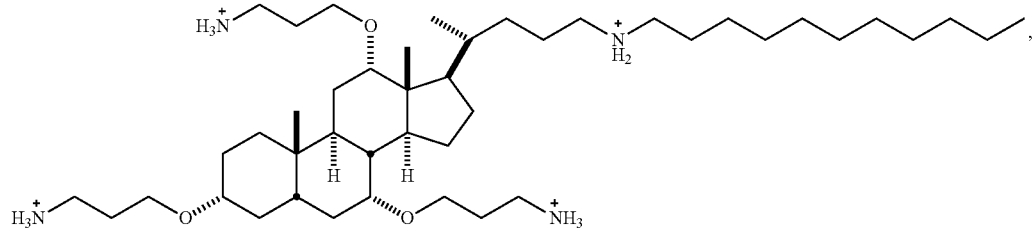
CSA-138
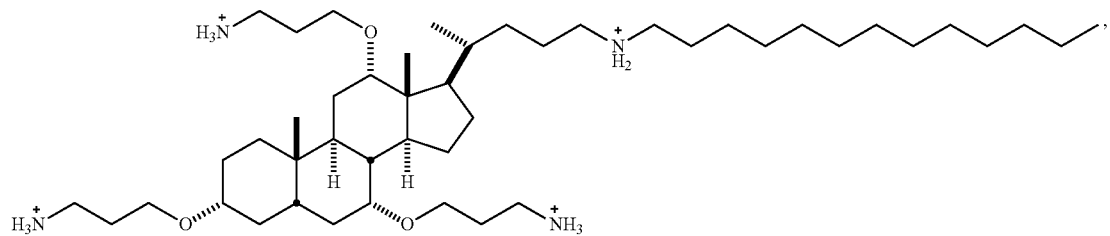

-continued

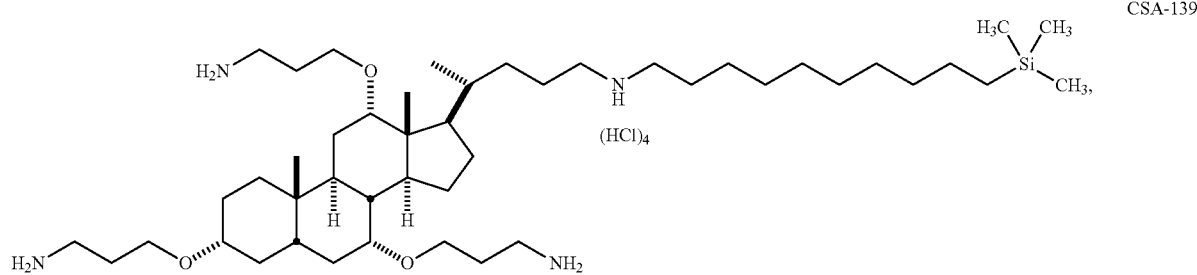
CSA-139

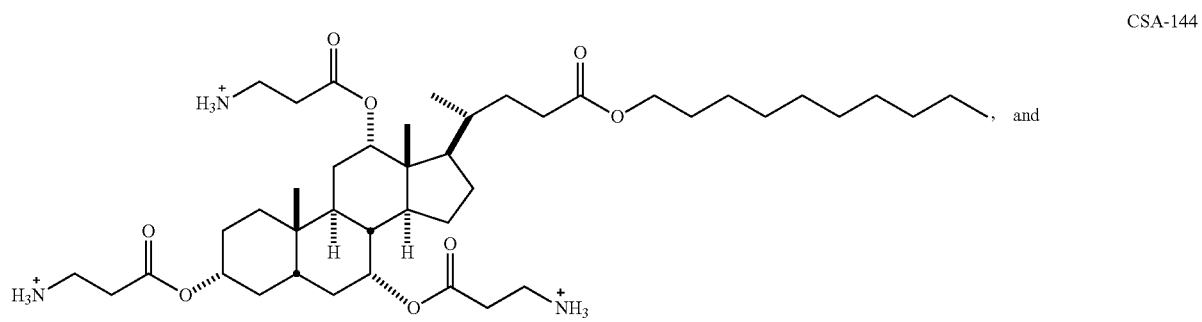
CSA-144

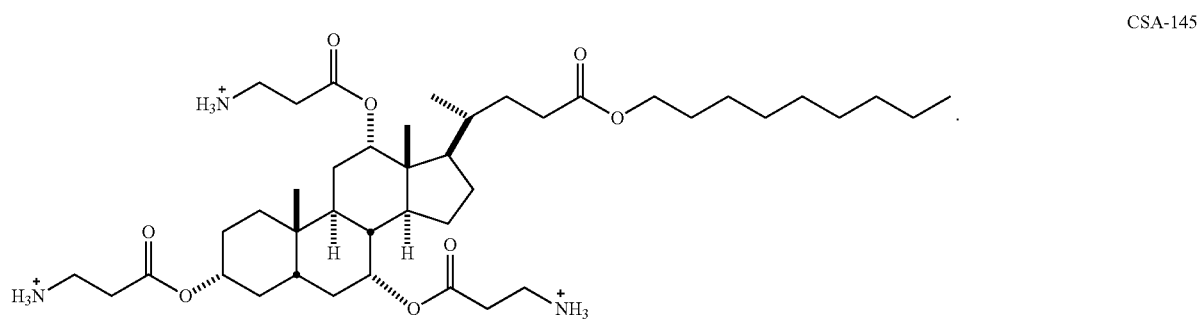
CSA-145

11. A device comprising a polymer structure and the hydrophobic CSA compound of claim 1 incorporated into the polymer structure with non-covalent interactions.

12. The device of claim 11, wherein the polymer structure comprises a polymer selected from the group consisting of polyvinyl alcohol, sodium polyacrylate, an acrylate polymer, polyethylene oxide, polyAMPS, polyvinylpyrrolidone, polyacrylamide, silicone, agarose, methylcellulose, hyaluronan, or a combination thereof.

13. The device of claim 11, wherein the device comprises a medical device selected from the group consisting of bone implant, bone pin, bone screw, tissue graft, endotracheal tube, coronary stent, peripheral stent, catheter, arterio-venous graft, by-pass graft, pacemaker or defibrillator lead, anastomotic clip, arterial closure device, patent foramen ovale closure device, and drug delivery balloon.

14. The device of claim 11, wherein the polymer structure includes a polymer coated on a substrate.

15. The device of claim 11, wherein the hydrophobic CSA compound elutes from the polymer structure in excess saline water at a rate of 0.1-100 µg/ml at 3 days.

16. A composition comprising at least one hydrophobic cationic steroidal anti-microbial (CSA) compound selected from the group consisting of:

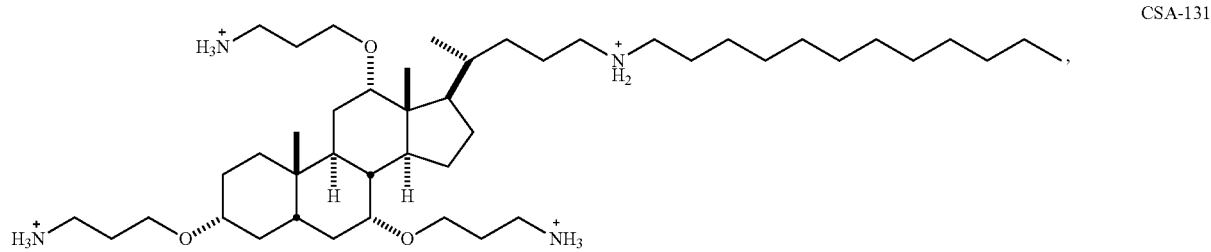
CSA-131

-continued
CSA-132
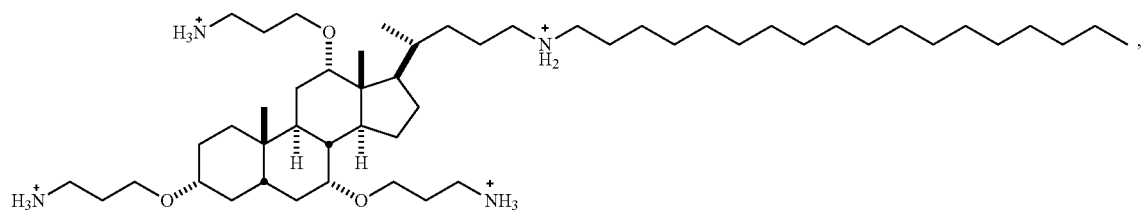
CSA-133
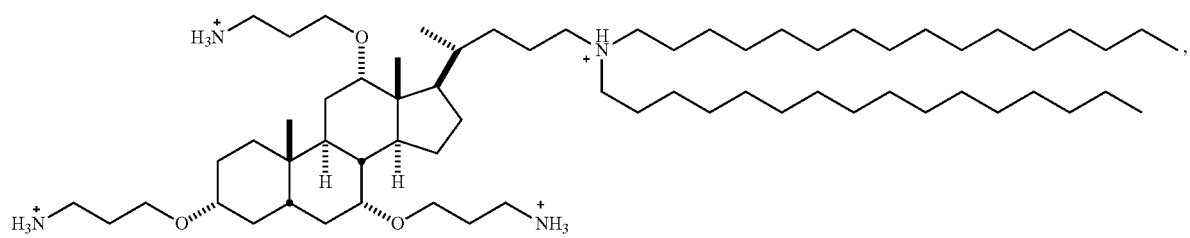
CSA-134
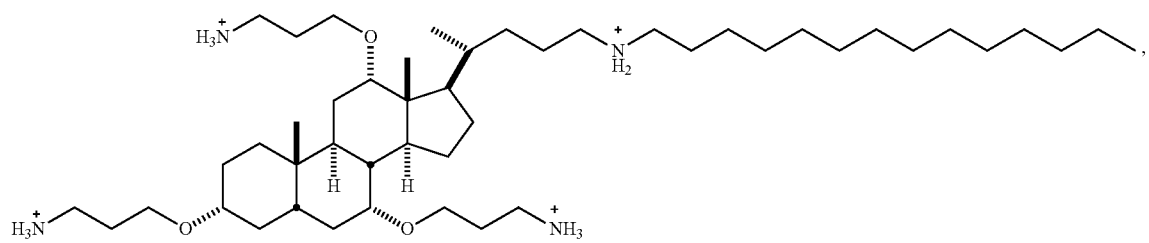
CSA-136
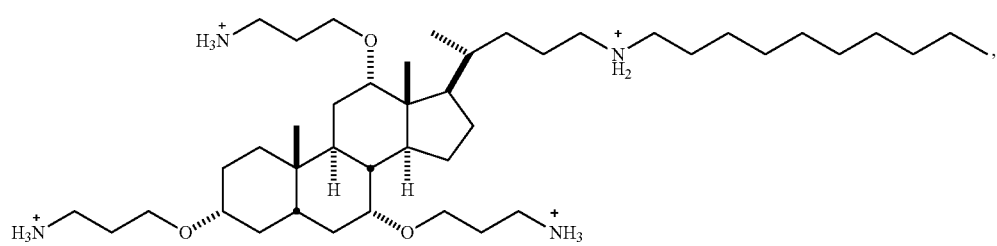
CSA-137
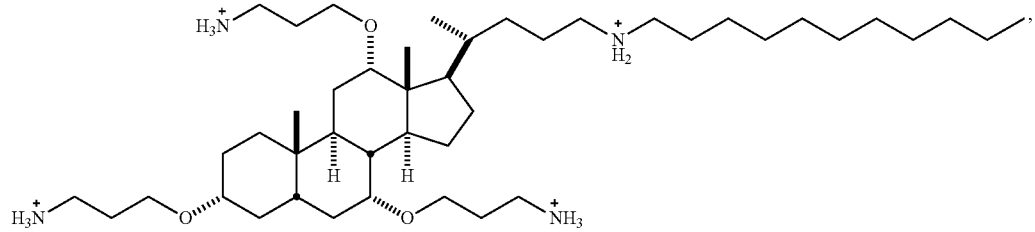
CSA-138
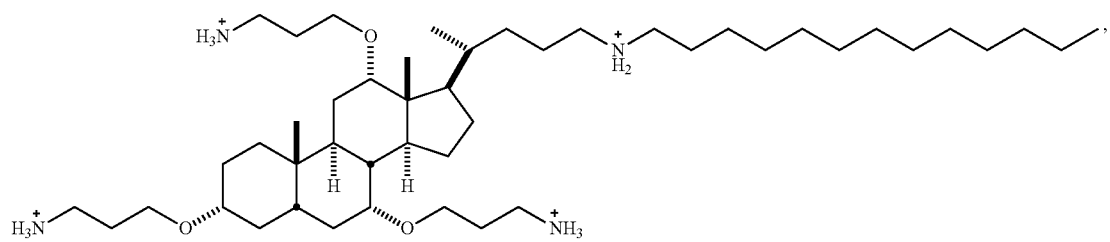

-continued
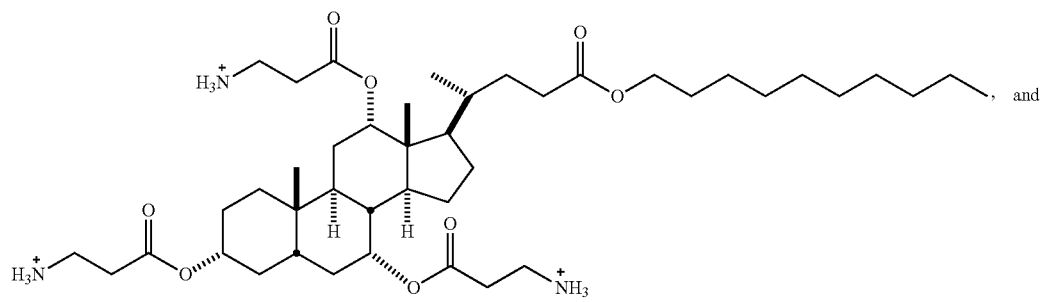
CSA-144
, and
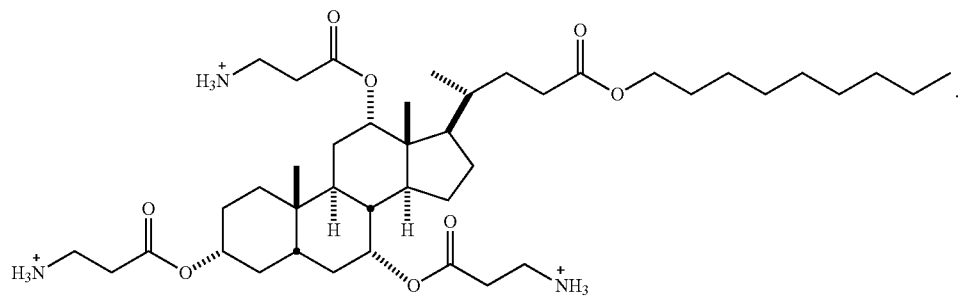
CSA-145
.
17. The composition of claim 16, wherein the at least one hydrophobic CSA compound is selected from the group consisting of:
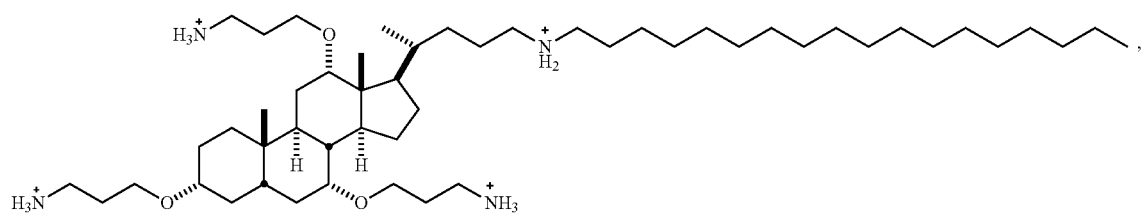
CSA-132
,
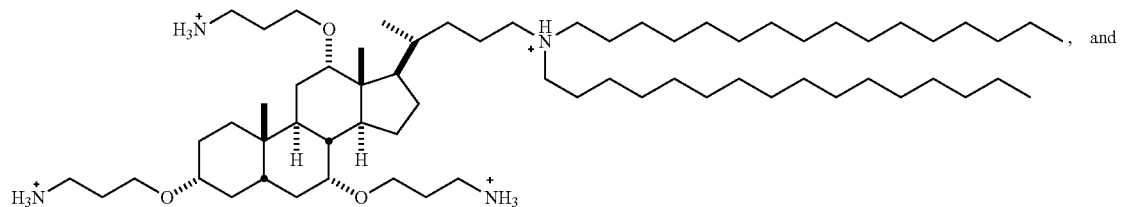
CSA-133
, and
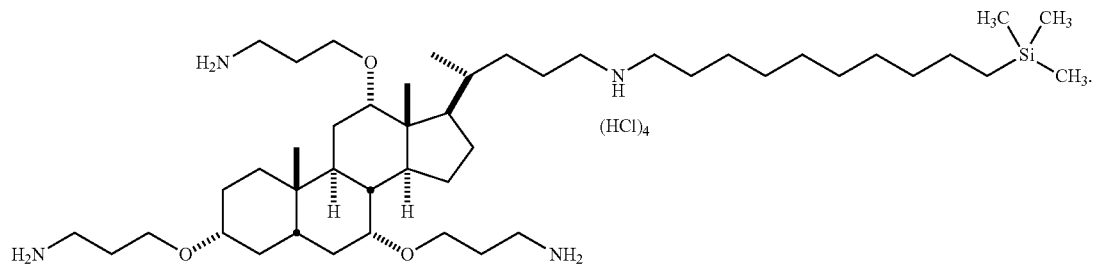
CSA-139
.

18. The composition of claim 16, wherein the at least one hydrophobic CSA compound comprises:
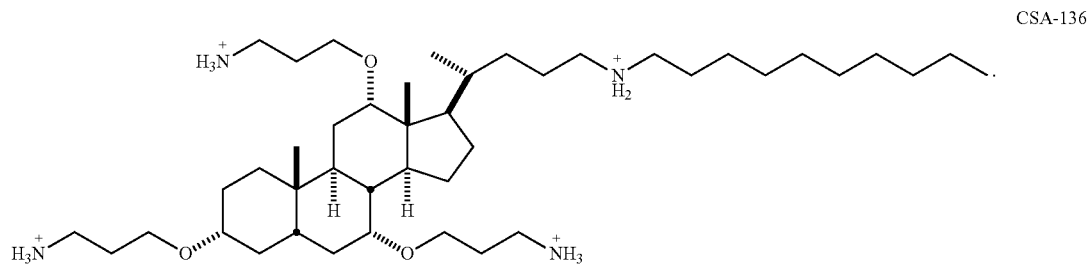
CSA-136
19. The composition of claim 16, wherein the at least one hydrophobic CSA compound comprises:
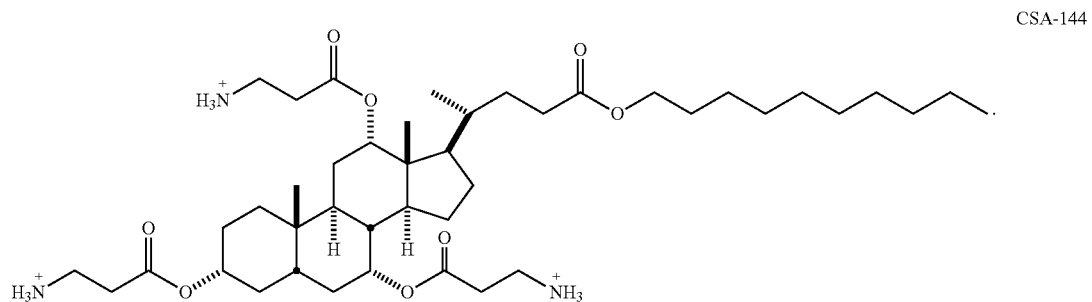
CSA-144
20. The composition of claim 16, wherein the at least one hydrophobic CSA compound comprises:
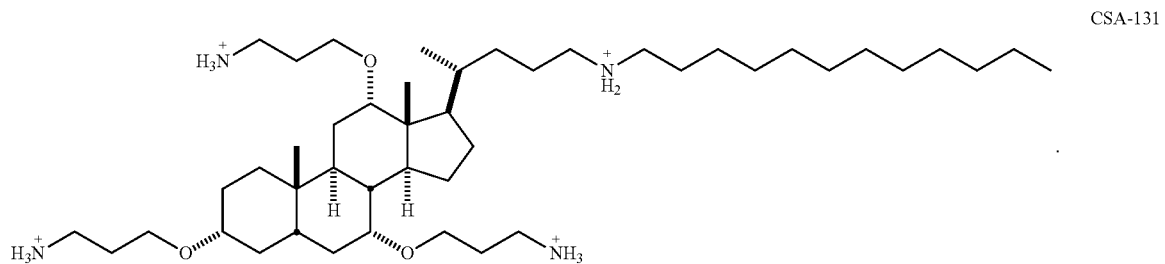
CSA-131
* * * * *

UNITED STATES PATENT AND TRADEMARK OFFICE
CERTIFICATE OF CORRECTION

| | |
|---|---|
| PATENT NO. | : 9,546,195 B2 |
| APPLICATION NO. | : 14/602499 |
| DATED | : January 17, 2017 |
| INVENTOR(S) | : Savage |

It is certified that error appears in the above-identified patent and that said Letters Patent is hereby corrected as shown below:

In the Drawings

Sheet 7, replace Fig. 2 with the figure depicted on the attached page, wherein the reference numbers --100--, --110--, and --120-- have been added In the Specification Column 4
Line 54, change "of a suitable" to --of suitable--

Column 8
Lines 7-8, change "hydrophilic (e.g. polyethyleneoxide)" to --hydrophilic chains (e.g. polyethyleneoxide)--
Line 9, change "polymer is a way" to --polymer in a way--
Line 46, change "incorporate" to --incorporating--

Column 9
Line 2, change "and therefore" to --and they therefore--
Line 18, change "non-covalently the functional" to --non-covalently with the functional--

Column 10
Line 38, insert --.-- after "these)"
Lines 60-61, change "on an out service" to --on an outer surface--

Signed and Sealed this
Eleventh Day of April, 2017

Michelle K. Lee
*Director of the United States Patent and Trademark Office*